US012410486B1

(12) United States Patent
Zhang et al.

(10) Patent No.: US 12,410,486 B1
(45) Date of Patent: Sep. 9, 2025

(54) PRIMER SET OF MYCOBACTERIUM TUBERCULOSIS BASED ON SPECIFIC HRCA ISOTHERMAL AMPLIFICATION AND AN APPLICATION THEREOF

(71) Applicant: Jiangsu University, Zhenjiang (CN)

(72) Inventors: Zhen Zhang, Zhenjiang (CN); Hu Zhang, Tai'an (CN); Kun Zeng, Zhenjiang (CN); Ming Li, Zhenjiang (CN)

(73) Assignee: Jiangsu University, Zhenjiang (CN)

( * ) Notice: Subject to any disclaimer, the term of this patent is extended or adjusted under 35 U.S.C. 154(b) by 0 days.

(21) Appl. No.: 19/083,413

(22) Filed: Mar. 18, 2025

(30) Foreign Application Priority Data

Jul. 8, 2024 (CN) .......................... 202410903484.4

(51) Int. Cl.
*C12Q 1/689* (2018.01)
*C12Q 1/6853* (2018.01)

(52) U.S. Cl.
CPC ........... *C12Q 1/689* (2013.01); *C12Q 1/6853* (2013.01)

(58) Field of Classification Search
CPC . C12Q 1/689; C12Q 1/6853; C12Q 2531/125
See application file for complete search history.

(56) References Cited

U.S. PATENT DOCUMENTS 11,028,435 B2 * 6/2021 Kelley ................. C12Q 1/6869
2008/0263730 A1 * 10/2008 Andersen ........... C12N 15/8261
536/23.6

OTHER PUBLICATIONS

Liu et al. Application of Hyperbranched Rolling Circle Amplification for Direct Detection of *Mycobacterium tuberculosis* in Clinical Sputum Specimens. PLoS One 2013; 8: e64583. (Year: 2013).*
Guo yan-ling et al., "Clinical application on rapid detection of *Mycobacterium tuberculosis* using Hyperbranched Rolling circle amplification", Journal of Clinical Pulmonary Medicine, May 2012, pp. 837-839, vol. 17 No. 5.

* cited by examiner

*Primary Examiner* — Angela M. Bertagna

(57) ABSTRACT

A primer set of *Mycobacterium tuberculosis* based on specific hyperbranched rolling circle amplification (HRCA) isothermal amplification includes: Lock and Key series primers for a recognition stage, and Loop and Link primers for an amplification stage. Using the primer set for an HRCA reaction enables rapid and sensitive detection with reliable and stable results. A method for detecting the *Mycobacterium tuberculosis* includes: (1) constructing a "lock" structure with recognition function; (2) performing magnetic selection and recognition; (3) conducting HRCA amplification; and (4) identifying a fluorescent signal to determine a positive or negative result determination. The method adopts the "lock" structure to design multiple conserved fragments of the *Mycobacterium tuberculosis* insertion sequence 6110 (IS6110) as target genes to jointly trigger the HRCA reaction, thereby enhancing the accuracy of the method.

2 Claims, 5 Drawing Sheets

Specification includes a Sequence Listing.

SEQUENCE LISTING

```
Sequence total quantity: 14
SEQ ID NO: 1            moltype = DNA  length = 50
FEATURE                 Location/Qualifiers
source                  1..50
                        mol_type = other DNA
                        organism = synthetic construct
SEQUENCE: 1
catcgaggag gtaatcaacc gggagcaatc ctgggctggc gccaactaat                50

SEQ ID NO: 2            moltype = DNA  length = 46
FEATURE                 Location/Qualifiers
source                  1..46
                        mol_type = other DNA
                        organism = synthetic construct
SEQUENCE: 2
tccacgatgg ccttatcgac ctactaaatg gggtcatgtc aaaaaa                    46

SEQ ID NO: 3            moltype = DNA  length = 32
FEATURE                 Location/Qualifiers
source                  1..32
                        mol_type = other DNA
                        organism = synthetic construct
SEQUENCE: 3
acctcctcga tgaaccacct gacatgaccc ca                                   32

SEQ ID NO: 4            moltype = DNA  length = 32
FEATURE                 Location/Qualifiers
source                  1..32
                        mol_type = other DNA
                        organism = synthetic construct
SEQUENCE: 4
gctcccggtt gatgtggtcg tagtaggtcg at                                   32

SEQ ID NO: 5            moltype = DNA  length = 32
FEATURE                 Location/Qualifiers
source                  1..32
                        mol_type = other DNA
                        organism = synthetic construct
SEQUENCE: 5
ggccatcgtg gaagcgaccc gccagcccag ga                                   32

SEQ ID NO: 6            moltype = DNA  length = 44
FEATURE                 Location/Qualifiers
source                  1..44
                        mol_type = other DNA
                        organism = synthetic construct
SEQUENCE: 6
gcgggtacct cctcgatgaa ccacctgaca tgaccccatc cttt                      44

SEQ ID NO: 7            moltype = DNA  length = 44
FEATURE                 Location/Qualifiers
source                  1..44
```

```
                        mol_type = other DNA
                        organism = synthetic construct
SEQUENCE: 7
ggctgggctc ccggttgatg tggtcgtagt aggtcgatgg ggcg                   44

SEQ ID NO: 8           moltype = DNA  length = 44
FEATURE                Location/Qualifiers
source                 1..44
                       mol_type = other DNA
                       organism = synthetic construct
SEQUENCE: 8
ggaggtggcc atcgtggaag cgacccgcca gcccaggatc ctgc                   44

SEQ ID NO: 9           moltype = DNA  length = 32
FEATURE                Location/Qualifiers
source                 1..32
                       mol_type = other DNA
                       organism = synthetic construct
SEQUENCE: 9
tggggtcatg tcaggtggtt catcgaggag gt                                32

SEQ ID NO: 10          moltype = DNA  length = 32
FEATURE                Location/Qualifiers
source                 1..32
                       mol_type = other DNA
                       organism = synthetic construct
SEQUENCE: 10
atcgacctac tacgaccaca tcaaccggga gc                                32

SEQ ID NO: 11          moltype = DNA  length = 32
FEATURE                Location/Qualifiers
source                 1..32
                       mol_type = other DNA
                       organism = synthetic construct
SEQUENCE: 11
tcctgggctg gcgggtcgct tccacgatgg cc                                32

SEQ ID NO: 12          moltype = DNA  length = 24
FEATURE                Location/Qualifiers
source                 1..24
                       mol_type = other DNA
                       organism = synthetic construct
SEQUENCE: 12
acctcctcga tgattagttg gcgc                                         24

SEQ ID NO: 13          moltype = DNA  length = 16
FEATURE                Location/Qualifiers
source                 1..16
                       mol_type = other DNA
                       organism = synthetic construct
SEQUENCE: 13
ctcccggttg attacc                                                  16

SEQ ID NO: 14          moltype = DNA  length = 16
FEATURE                Location/Qualifiers
source                 1..16
                       mol_type = other DNA
                       organism = synthetic construct
SEQUENCE: 14
cgccagccca ggattg                                                  16
```

PRIMER SET OF MYCOBACTERIUM TUBERCULOSIS BASED ON SPECIFIC HRCA ISOTHERMAL AMPLIFICATION AND AN APPLICATION THEREOF

CROSS-REFERENCE TO RELATED APPLICATION

This application claims priority to Chinese Patent Application No. 202410903484.4, filed Jul. 8, 2024, which is herein incorporated by reference in its entirety.

TECHNICAL FIELD

The disclosure relates to the field of biotechnologies, and more particularly to a primer set of *Mycobacterium tuberculosis* based on specific hyperbranched rolling circle amplification (HRCA) isothermal amplification and an application thereof.

STATEMENT REGARDING SEQUENCE LISTING

The sequence listing associated with this application is provided in text format in lieu of a paper copy and is hereby incorporated by reference into the specification. The name of the XML file containing the sequence listing is 25011THXT-USP1-US-2025-0006-SL.xml. The XML file is 13,612 bytes; is created on Mar. 12, 2024; and is being submitted electronically via patent center.

BACKGROUND

*Mycobacterium tuberculosis* is a pathogen of tuberculosis. Early diagnosis and timely treatment are a key to effectively control the spread of tuberculosis and restore the health of tuberculosis patients.

HRCA is a novel technology in vitro nucleic acid amplification that requires a lower temperature requirement. It does not need expensive and sophisticated temperature cycling equipment and can be completed at a constant temperature. Utilizing the HRCA technology for the detection of *Mycobacterium tuberculosis* helps to reduce the complexity of a detection procedure, shorten a detection time, and lower detection cost. Moreover, it does not rely on specific instruments, and results can be read with the naked eye.

However, such molecular detection technology is prone to false-positive and false-negative results due to the influence of selected insertion sequence targets. Moreover, the technology itself may also exhibit non-specific amplification, which can lead to false-positive outcomes. Based on this, a primer set of *Mycobacterium tuberculosis* based on specific HRCA isothermal amplification and an application thereof are provided by the disclosure.

SUMMARY

For the above technical problems, a purpose of the disclosure is to provide a highly specific HRCA method for detecting *Mycobacterium tuberculosis*. Utilizing this method, detection results of the *Mycobacterium tuberculosis* are reliable and stable.

Specifically, the disclosure can adopt the following technical solutions.

In a first aspect, the disclosure provides a primer set of *Mycobacterium tuberculosis* based on specific HRCA isothermal amplification, the primer set includes Loop primer, Mag primer, Lock1 primer, Lock2 primer, Lock3 primer, Seal primer, Branch1 primer and Branch2 primer.

The nucleotide sequence of the Loop primer is shown in SEQ ID NO: 1, and a 5' end of the Loop primer is phosphorylated.

The nucleotide sequence of the Mag primer is shown in SEQ ID NO: 2, and a 3' end of the Mag primer is biotinylated.

The nucleotide sequences of the Lock1 primer, the Lock2 primer, and the Lock3 primer are shown in SEQ ID NO: 3 to SEQ ID NO: 5, respectively.

The nucleotide sequence of the Seal primer is shown in SEQ ID NO: 12.

The nucleotide sequences of the Branch1 primer and the Branch2 primer are shown in SEQ ID NO: 13 and SEQ ID NO: 14, respectively.

In an embodiment, the primer set further includes a recognition primer set, the recognition primer set includes Block1, Block2, Block3, Key1, Key2, and Key 3; and the nucleotide sequences of the Block1, the Block2, and the Block3 are shown in SEQ ID NO: 6 to SEQ ID NO: 8, respectively, and the nucleotide sequences of the Key1, the Key2, and the Key3 are shown in SEQ ID NO: 9 to SEQ ID NO: 11, respectively.

In a second aspect, the disclosure provides a detection kit for detecting the *Mycobacterium tuberculosis*, and the detection kit includes the primer set of the *Mycobacterium tuberculosis* provided in the first aspect of the disclosure.

In a third aspect, the disclosure provides a method for detecting the *Mycobacterium tuberculosis* using the primer set described in the first aspect or the detection kit described in the second aspect.

In an embodiment, the method includes the following steps:

- step 1), annealing the Loop primer, the Mag primer, the Lock1 primer, the Lock2 primer, and the Lock3 primer to synthesize a "lock" structure;
- step 2), mixing and incubating the "lock" structure obtained in the step 1) with dispersed magnetic beads to fix the "lock" structure on the dispersed magnetic beads, thereby to obtain a magnetic bead-primer mixture;
- step 3), mixing and incubating a sample to be tested with the recognition primer set to obtain an incubated sample;
- step 4), mixing the incubated sample obtained in the step 3) with the magnetic bead-primer mixture prepared in the step 2) to complete a "unlocking" process, and performing magnetic separation on the Loop primer;
- step 5), adding the Seal primer and ligase to perform circularization of the Loop primer with a sealing system;
- step 6), adding the Branch1 primer and the Branch2 primer to polymerase to perform an HRCA reaction with a reaction system; and
- step 7), adding calcein to read a fluorescence signal of the reaction system, and determining a positive signal or negative signal determination.

In an embodiment, the Loop primer in the "lock" structure can bind to the Seal primer and be circularized under an action of the ligase, thereby triggering the HRCA reaction downstream.

In an embodiment, a concentration of the "lock" structure mixed with the dispersed magnetic beads is 200 nanomoles per liter (nM).

In an embodiment, after the Loop primer is circularized, the Loop primer performs the HRCA reaction together with Branch primers.

In an embodiment, a temperature of the annealing in the step 1) is 95° C., and a time of the annealing in the step 1) is 10 minutes. After the annealing, the "lock" structure is stored at 4° C.

In an embodiment, in the step 5), the ligase is T4 bacteriophage deoxyribonucleic acid (T4 DNA) ligase.

In an embodiment, in the step 5), the sealing system includes: a final concentration of tris(hydroxymethyl)aminomethane (Tris) of 40 millimoles per liter (mM), a final concentration of magnesium chloride ($Mg_2Cl_2$) of 10 mM, a final concentration of dithiothreitol (DDT) of 10 mM, a final concentration of adenosine triphosphate (ATP) of 1 mM, and a final concentration of T4 DNA ligase of 0.5 units per microliter (U/μL).

In an embodiment, the circularization of the Loop primer is performed at 37° C. for 30 minutes, followed by inactivating the T4 DNA ligase at 65° C. for 10 minutes.

In an embodiment, the reaction system in the step 6) includes: a final concentration of tris(hydroxymethyl)aminomethane hydrochloride (Tris-HCl) of 18 mM to 22 mM, specifically 20 mM; a final concentration of ammonium sulfate (($NH_4)_2SO_4$) of 8 mM to 12 mM, specifically 10 mM; a final concentration of potassium chloride (KCl) of 8 mM to 12 mM, specifically 10 mM; a final concentration of magnesium sulfate ($MgSO_4$) of 55 mM to 65 mM, specifically 60 mM; a final concentration of ethylenediaminetetraacetic acid (EDTA) of 0.08 mM to 0.12 mM, specifically 0.1 mM; a final concentration of DTT of 0.8 mM to 1.2 mM, specifically 1 mM; a final concentration of polyethylene glycol octylphenyl ether (Triton X-100) of 0.08% to 0.12%, specifically 0.1%; a final concentration of glycerol of 1% to 3%, specifically 2%; a final concentration of branch primer pair of 0.08 micromoles per liter (μM) to 0.12 μM, specifically 0.1 μM; a final concentration of deoxyribonucleoside triphosphates (dNTPs) of 0.8 mM to 1.2 mM, specifically 1 mM; and a final concentration of *Bacillus stearothermophilus* deoxyribonucleic (Bst DNA) polymerase of 300 U/μL to 350 U/μL, specifically 320 U/μL.

In an embodiment, in the step 6), the HRCA reaction is performed at 60° C. to 68° C. for 0.8 hours to 1.2 hours. Specifically, the HRCA reaction is performed at 65° C. for 1 hour, followed by inactivating the Bst DNA polymerase at 75° C. to 85° C. for 8 minutes to 12 minutes. Specifically, the inactivating is performed at 80° C. for 10 minutes.

In an embodiment, in the step 6), when the calcein is used as an indicator, under visible light, a light yellow color indicates a positive result, and a light pink color indicates a negative result; under ultraviolet light, green fluorescence indicates a positive result, and absence of fluorescence indicates a negative result.

Compared to the related art, the disclosure, adopting the above-mentioned solutions, has the following advantages.

(1) The primer set provided by the disclosure is divided into two parts: recognition and amplification. The recognition part is designed based on an insertion sequence 6110 (IS6110) of the *Mycobacterium tuberculosis*, adopting a "many-to-one" approach to identify a target gene. Multiple primers are used to form a structure similar to a "lock", which enhances the specificity of target gene recognition and ensures accurate identification of the *Mycobacterium tuberculosis*. The amplification part is designed using the Loop primer as a template, and amplification is triggered only when the *Mycobacterium tuberculosis* is recognized. The detection of the *Mycobacterium tuberculosis* using the above primer set is highly sensitive and specific.

(2) The "lock" structure designed by the disclosure requires multiple characteristic sequences of the *Mycobacterium tuberculosis* to be activated, which in turn triggers the HRCA reaction downstream, thereby enhancing the accuracy of the detection.

(3) A specific amplification primer is designed for the *Mycobacterium tuberculosis*, and an HRCA method is adopted for the detection of the *Mycobacterium tuberculosis*. This method reduces detection time and saves on production and testing costs. It offers good sensitivity and strong specificity, providing a sensitive, accurate, and low-cost detection solution.

BRIEF DESCRIPTION OF DRAWINGS

In order to more clearly illustrate the technical solutions of the embodiments of the disclosure, the accompanying drawings necessary for the embodiments will be briefly introduced below. It should be understood that the accompanying drawings set forth below merely illustrate some embodiments of the disclosure and are not intended to limit the scope of the disclosure. For those skilled in the art, other relevant drawings can be obtained based on these drawings without making any inventive effort.

FIG. 2A illustrates a schematic diagram of magnetic beads with different coating densities, and FIG. 2B illustrates fluorescence intensity under the different magnetic bead coating densities.

FIG. 3A illustrates optimization of HRCA reaction time, FIG. 3B illustrates optimization of an addition amount of T4 DNA ligase, FIG. 3C illustrates optimization of an addition amount of Bst DNA polymerase, and FIG. 3D illustrates optimization of a final concentration of dNTPs in a system.

DETAILED DESCRIPTION OF EMBODIMENTS

To make the purposes, technical solutions, and advantages of the embodiments of the disclosure clearer, the technical solutions of the embodiments will be described clearly and completely below in conjunction with the accompanying drawings of the embodiments. It should be apparent that the described embodiments are only a part of the embodiments of the disclosure, and not all of them. All other embodiments obtained by those skilled in the art without making any inventive effort based on the embodiments described herein are within the scope of protection of the disclosure.

Embodiment 1 design of a primer set

The primer set for detecting *Mycobacterium tuberculosis* is shown in Table 1.

TABLE 1 the primer set for detecting the *Mycobacterium tuberculosis*

| primer | Primer sequence (5'-3') | SEQ ID NO |
|---|---|---|
| Loop | CATCGAGGAGGTAATCAAC CGGGAGCAATCCTGGGCTG GCGCCAACTAAT | SEQ ID NO: 1 |
| Mag | TCCACGATGGCCTTATCGA CCTACTAAATGGGGTCATG TCAAAAAA | SEQ ID NO: 2 |
| Lock1 | ACCTCCTCGATGAACCACC TGACATGACCCCA | SEQ ID NO: 3 |
| Lock2 | GCTCCCGGTTGATGTGGTC GTAGTAGGTCGAT | SEQ ID NO: 4 |
| Lock3 | GGCCATCGTGGAAGCGACC CGCCAGCCCAGGA | SEQ ID NO: 5 |
| Block1 | GCGGGTACCTCCTCGATGA ACCACCTGACATGACCCCA TCCTTT | SEQ ID NO: 6 |
| Block2 | GGCTGGGCTCCCGGTTGAT GTGGTCGTAGTAGGTCGAT GGGGCG | SEQ ID NO: 7 |
| Block3 | GGAGGTGGCCATCGTGGAA GCGACCCGCCAGCCCAGGA TCCTGC | SEQ ID NO: 8 |
| Key1 | TGGGGTCATGTCAGGTGGT TCATCGAGGAGGT | SEQ ID NO: 9 |
| Key2 | ATCGACCTACTACGACCAC ATCAACCGGGAGC | SEQ ID NO: 10 |
| Key3 | TCCTGGGCTGGCGGGTCGC TTCCACGATGGCC | SEQ ID NO: 11 |
| Seal | ACCTCCTCGATGATTAGTT GGCGC | SEQ ID NO: 12 |
| Branch1 | CTCCCGGTTGATTACC | SEQ ID NO: 13 |
| Branck2 | CGCCAGCCCAGGATTG | SEQ ID NO: 14 |

Figure 1:
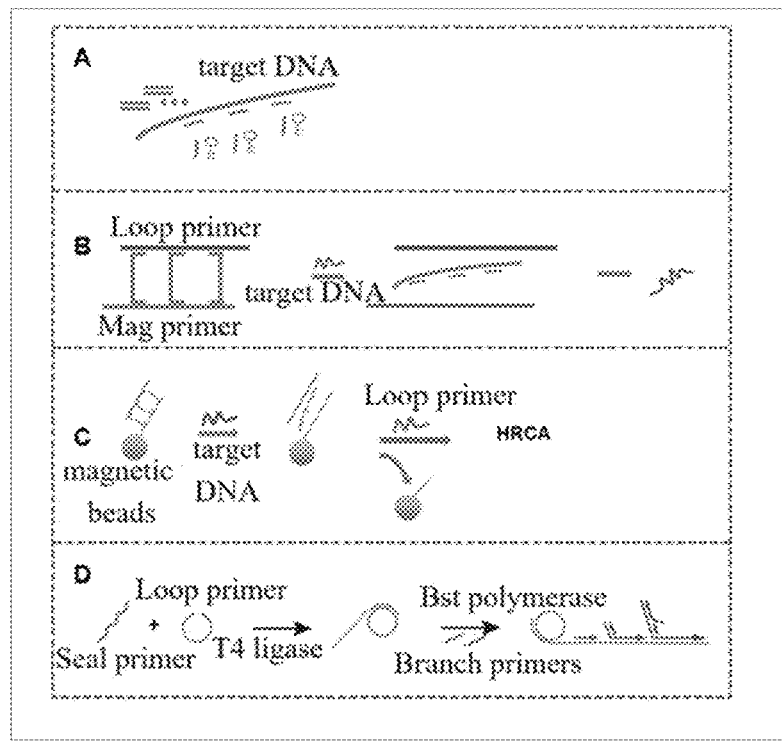
FIG. 1 illustrates a schematic diagram of a method for detecting *Mycobacterium tuberculosis* based on HRCA. Specifically, in FIG. 1, A illustrates a target DNA, B illustrates a reaction process of a complex structure of a Loop primer and a Mag primer with the target DNA; C illustrates a process of capturing the target DNA with magnetic beads and releasing the Loop primer; and D illustrates an HRCA reaction of a circular Loop primer with Branch primers and Bst polymerase.

Embodiment 2 a method for detecting the *Mycobacterium tuberculosis* based on specific HRCA, as shown in FIG. 1, includes the following steps.

Step 1), recognition of a target gene: genetic material of the *Mycobacterium tuberculosis* after lysis is extracted. The genetic material is mixed with a primer set consisting of Block1, Block2, Block3, Key1, Key2, and Key3 at a concentration of 200 nM to obtain a mixed solution. The mixed solution is heated at 95° C. for 5 minutes and then placed on ice for 10 minutes.

Step 2), synthesis of a "lock" structure: a primer set consisting of Loop primer, Mag primer, Lock1 primer, Lock2 primer, and Lock3 primer is added to a tris-magnesium (TAMg) buffer solution in a tube to obtain a TAMg buffer mixture. A final concentration of the TAMg buffer mixture is 500 nM. The TAMg buffer mixture is heated at 95° C. for 10 minutes and then annealed in a refrigerator at 4° C. for 1 hour. Then the TAMg buffer mixture is combined with dispersed magnetic beads and gently shaken by inverting the tube. The mixture is then incubated at room temperature for 1 hour (with gentle mixing every 15 minutes). After incubation, magnetic beads are collected using a magnetic separation rack, and supernatant is discarded. The magnetic beads are washed five times with 100 microliters (μL) of phosphate buffered saline (PBS) buffer solution.

The TAMg buffer solution includes 45 mM of Tris-Base, and 12.5 mM of $MgCl_2$, and a pH of the TAMg buffer solution is 8.

Step 3), the mixed solution in the step 1) is mixed with the magnetic beads prepared in the step 2) to obtain a magnetic beads-primer mixture. The magnetic beads-primer mixture is reacted at 37° C. for 30 minutes to allow key primers to release the Loop primer, and then supernatant is extracted by performing magnetic separation.

Step 4), circularization of the Loop primer: 20 μL of the supernatant obtained in the step 3) is mixed with 2.5 μL of 10×T4 Buffer from New England Biolabs (Beijing, China), 2 μL of the Seal primer at a concentration of 2.5 μM, and 0.5 μL of T4 DNA ligase at a concentration of 25 U/μL to obtain a supernatant mixture. The supernatant mixture is reacted at 37° C. for 30 minutes to circularize the Loop primer and then reacted at 65° C. for 10 minutes to inactivate the T4 DNA ligase.

Step 5), HRCA reaction: on the basis of the above system, 5 μL of 10×ThermoPOL Buffer from New England Biolabs (Beijing, China), 3 μL of $MgSO_4$ at a concentration of 100 mM, 5 μL of dNTP mixed solution at a concentration of 10 mM, 5 μL each of the Branch1 primer and the Branch2 primer each at a concentration of 1 μM, and 2 μL of Bst DNA polymerase stocked solution are added and mixed to obtain a mixed solution. The mixed solution is incubated at 65° C. for 1 hour to perform an HRCA reaction, and then incubated at 80° C. for 20 minutes to inactivate Bst DNA polymerase.

Step 6), calcein staining: calcein at a final concentration of 0.05 mM and $MnCl_2$ at a final concentration of 0.6 mM are added to the supernatant mixture after reaction from the step 4). The system is sealed with paraffin oil and incubated at 65° C. for 60 minutes. A color change of a reaction tube before and after the HRCA reaction is observed, negative results appear light orange, and positive results appear light green.

An excitation wavelength for reading fluorescence of the calcein is 490 (nanometers) nm to 500 nm.

Embodiment 3 optimization of magnetic bead coating density in the method

Figure 2A:
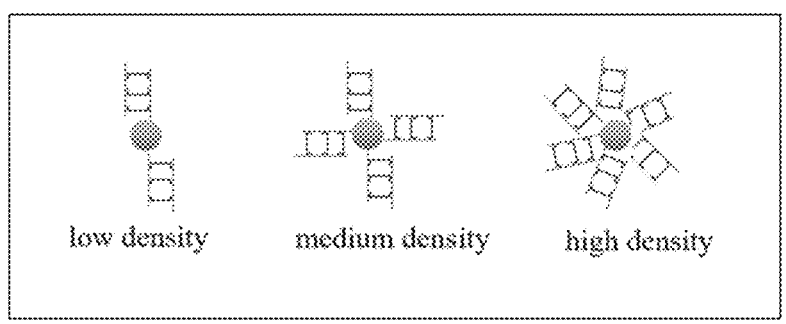
FIGS. 2A-2B illustrate effects of different magnetic bead coating densities on detection. Specifically.
Figure 2B:
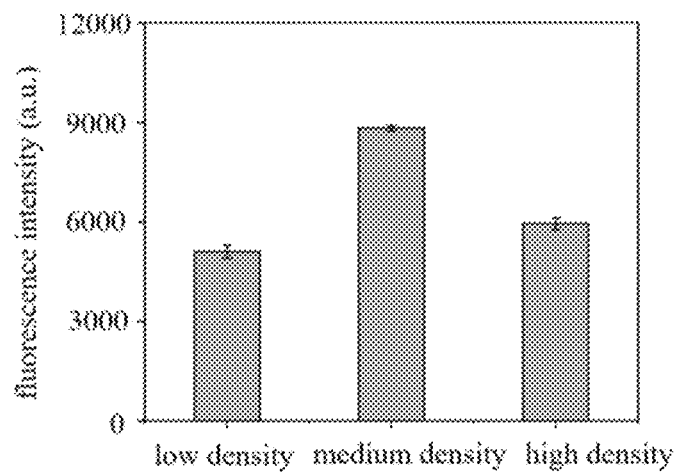

To verify effects of different magnetic bead coating densities on detection results, three different concentrations of 100 nM, 200 nM, and 400 nM of the "lock" structure are mixed with the dispersed magnetic beads to obtain mixtures. The mixtures are gently shaken by inverting tubes, and binding states of primers with different concentrations to the dispersed magnetic beads are shown in FIG. 2A. After incubation at room temperature for 1 hour (with shaken every 15 minutes), the magnetic beads are collected using the magnetic separation rack, and the supernatant is discarded. The magnetic beads are then washed five times with 100 μL of the PBS buffer solution. The detection results for each magnetic bead coating density are subsequently tested. The detection results are shown in FIG. 2B. Based on these results, magnetic beads with medium coating density are selected for subsequent experiments.

Embodiment 4 optimization of reaction conditions in the method

Figure 3A:
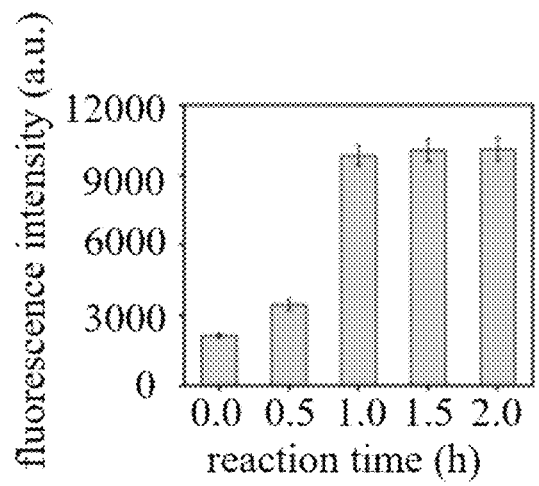
FIGS. 3A-3D illustrate optimization of reaction conditions in the method for detecting the *Mycobacterium tuberculosis* using the primer set of the *Mycobacterium tuberculosis* based on the specific HRCA isothermal amplification. Specifically.
Figure 3B:
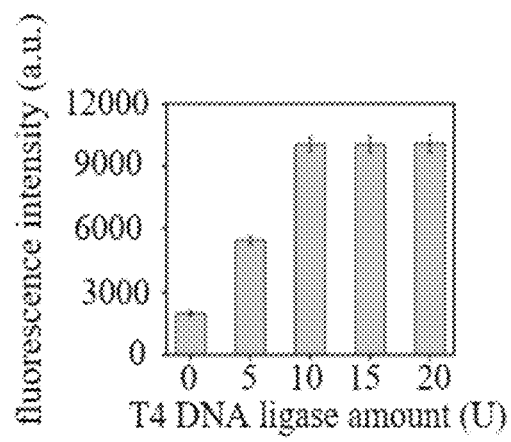
Figure 3C:
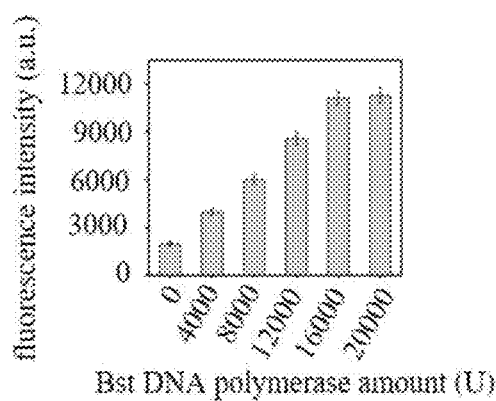
Figure 3D:
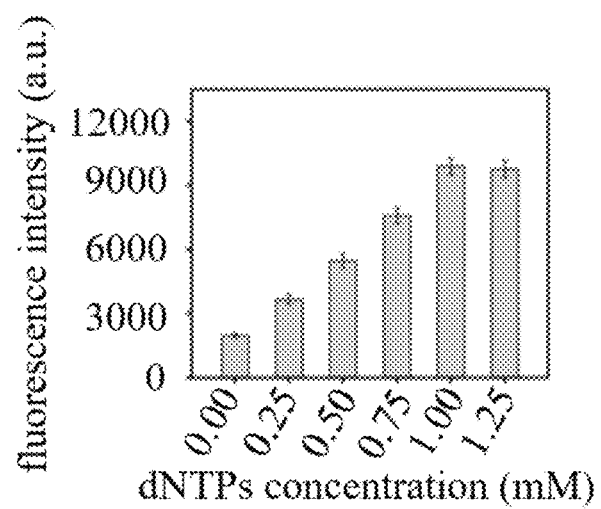

To achieve the optimal reaction performance, an HRCA reaction time (shown in FIG. 3A), an addition amount of the T4 DNA ligase (shown in FIG. 3B), an addition amount of Bst DNA polymerase (shown in FIG. 3C), and a final concentration of dNTPs (shown in FIG. 3D) are optimized for the proposed method. Based on optimization results, the HRCA reaction time is set to 1 hour, the addition amount of the T4 DNA ligase is 10 units (U), the addition amount of the Bst DNA polymerase is 16,000 U, and the final concentration of the dNTPs is 1 mM.

Embodiment 5 validation of detection performance in the method

Figure 4:
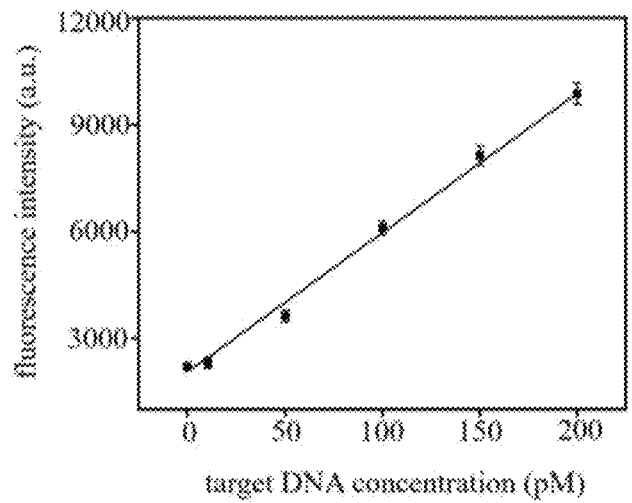
FIG. 4 illustrates a standard curve diagram of target DNA with different concentrations.

To validate the detection performance of the proposed method, detection sensitivity is evaluated by testing target DNA at various concentrations after optimizing the reaction conditions. Results are shown in FIG. 4. No signal is detected when a concentration of the target DNA is below 10 picomoles per liter (pM). A good linear relationship is observed between 10 pM and 200 pM. Based on a 3-sigma (3σ) method, a calculated detection limit is as low as 3.2 pM.

Embodiment 6 validation of selectivity in the method

Figure 5:
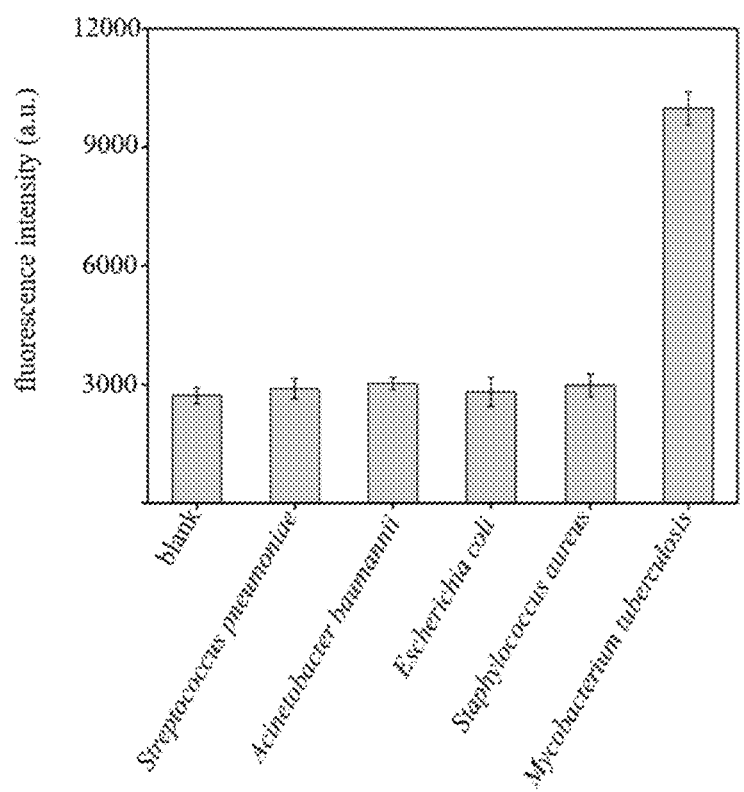
FIG. 5 illustrates a diagram of selectivity in the method for detecting the *Mycobacterium tuberculosis* using the primer set of the *Mycobacterium tuberculosis* based on the specific HRCA isothermal amplification.

To verify selectivity of the method for the *Mycobacterium tuberculosis*, genomic DNAs extracted from *Streptococcus pneumoniae*, *Acinetobacter baumannii*, *Escherichia coli*, *Staphylococcus aureus*, and the *Mycobacterium tuberculosis* are tested, with an additional control group. Test results are shown in FIG. 5. The test results illustrate that a strong signal is only detected in the presence of *Mycobacterium tuberculosis* DNA, indicating that the method has good selectivity.

The above description is merely a specific embodiment of the disclosure, enabling those skilled in the art to understand or implement the disclosure. Various modifications to these embodiments will be obvious to those skilled in the art, and the general principles defined in this text can be realized in other embodiments without departing from the spirit or scope of the disclosure. Therefore, the disclosure is not limited to the embodiments illustrated herein, but is to be accorded the broadest scope consistent with the principles and novel features disclosed herein.

---

What is claimed is:

1. A primer set for detecting *Mycobacterium tuberculosis* based on specific hyperbranched rolling circle amplification (HRCA) isothermal amplification, wherein the primer set comprises a Loop primer, a Mag primer, a Lock1 primer, a Lock2 primer, a Lock3 primer, a Seal primer, a Branch1 primer and a Branch2 primer;

wherein the nucleotide sequence of the Loop primer is shown in SEQ ID NO: 1;

wherein the nucleotide sequence of the Mag primer is shown in SEQ ID NO: 2;

wherein the nucleotide sequences of the Lock1 primer, the Lock2 primer, and the Lock3 primer are shown in SEQ ID NO: 3 to SEQ ID NO: 5, respectively;

wherein the nucleotide sequence of the Seal primer is shown in SEQ ID NO: 12;

wherein the nucleotide sequences of the Branch1 primer and the Branch2 primer are shown in SEQ ID NO: 13 and SEQ ID NO: 14, respectively; and wherein the primer set further comprises a recognition primer set, and the recognition primer set comprises Block1, Block2, Block3, Key1, Key2, and Key 3; and the nucleotide sequences of Block1, Block2, and Block3 are shown in SEQ ID NO: 6 to SEQ ID NO: 8, respectively, and the nucleotide sequences of Key1, Key2, and Key3 are shown in SEQ ID NO: 9 to SEQ ID NO: 11, respectively.

2. A detection kit for detecting *Mycobacterium tuberculosis*, wherein the detection kit comprises the nucleotide sequences shown in SEQ ID NOs: 1-14 in the primer set as claimed in claim 1.

\* \* \* \* \*